United States Patent [19]

Goldstein

[11] Patent Number: 4,920,982

[45] Date of Patent: May 1, 1990

[54] PERCUTANEOUS VASECTOMY METHOD

[75] Inventor: Marc Goldstein, New York, N.Y.

[73] Assignee: Vastech Medical Products Inc., New Brunswick, N.J.

[21] Appl. No.: 211,574

[22] Filed: Jun. 27, 1988

[51] Int. Cl.$^5$ .............................................. A61F 13/00
[52] U.S. Cl. ........................................ 128/842; 606/49
[58] Field of Search ......... 128/303 A, 303.17, 303.18, 128/784, 794, 842, 843

[56] References Cited

U.S. PATENT DOCUMENTS

| | | | |
|---|---|---|---|
| 3,974,833 | 8/1976 | Durden | 128/303.17 |
| 4,034,762 | 7/1977 | Cosers et al. | 128/303.17 |
| 4,085,756 | 4/1978 | Weaver | 128/303.17 |
| 4,103,688 | 8/1978 | Edwards | 128/303.17 |
| 4,269,174 | 5/1981 | Adair | 128/842 |
| 4,493,319 | 1/1985 | Polk et al. | 128/303 A |

OTHER PUBLICATIONS

Li Shun-qiang, Zhu Jin-bo, "Non-Operative Sterility Research with Intravasal Injecting Drug", Family Planning Research Institute of Chungqing, China, 1984.
Li Shunqiang, "Clinical Application of Vas Deferens Puncture," The First Worker's Hospital of Chongqing, Sichuan, China, 1980.

Primary Examiner—Max Hindenburg
Attorney, Agent, or Firm—Lerner, David, Littenberg, Krumholz & Mentlik; 13

[57] ABSTRACT

A percutaneous vasectomy method is disclosed which involves closing the vas deferens of a male patient without incising the patient's scrotum. The method comprises the steps of inserting a sharp-tipped needle having a first predetermined diameter into the scrotum of the male patient and through a wall of the vas deferens, the insertion forming a passageway from the surface of the scrotum to the interior of the vas deferens; removing the sharp-tipped needle from the vas deferens and the scrotum; inserting a blunt-tipped needle having a second predetermined diameter, less than the first predetermined diameter, through the passageway and into the interior of the vas deferens; activating a cauterizing element which includes the blunt-tipped needle for a selected period of time to cauterize and thereby close the vas deferens to sterilize the male patient; and removing the blunt-tipped needle from the vas deferens and scrotum.

6 Claims, 4 Drawing Sheets

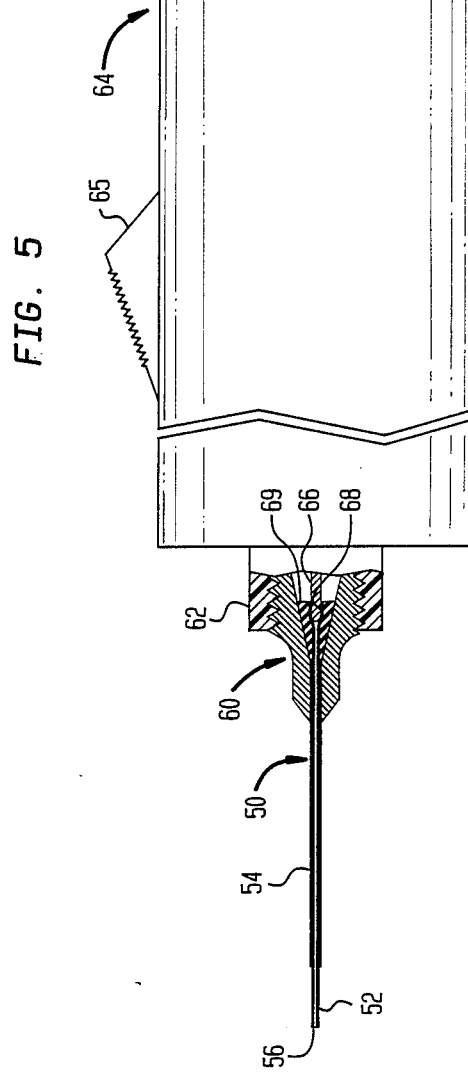
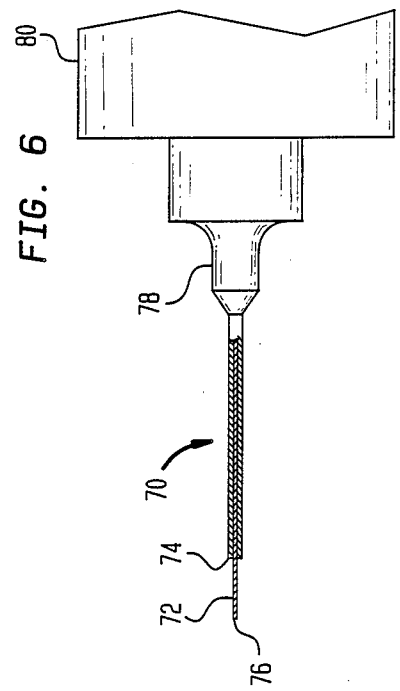

PERCUTANEOUS VASECTOMY METHOD

FIELD OF THE INVENTION

This invention relates to a method for sterilizing a male patent and, more particularly, to a method of cauterizing the patient's vas deferens without making an incision in the wall of the patient's scrotum.

BACKGROUND OF THE INVENTION

Male sterilization is generally accomplished by vasectomy in which the vas deferens is surgically interrupted by ligation or by cauterization. This procedure generally requires surgical opening of the scrotum. Although vasectomy is simpler, safer and less expensive than female sterilization, far fewer male sterilizations are performed world-wide than female sterilizations due, at least in part, to an excessive apprehension of the pain that might be associated with such a procedure. In addition, in many parts of the world, males equate any surgical procedure performed on male genitals to castration.

One example of a patent which shows apparatus and methods for performing vasectomy procedures in which the scrotum is surgically opened is U.S. Pat. No. 4,103,688 to Edwards. In Edwards, an incision is first made in the scrotum and then the vas deferens is severed. Next, the uninsulated tip of a unipolar needle electrode is sequentially inserted into the openings of the severed ends of the vas deferens to cauterize the ends. Similarly, in U.S. Pat. No. 4,034,762 to Cosens, et al., incisions are first made in the scrotum and in the vas deferens and then a bipolar needle electrode is inserted into the severed ends of the vas deferens to seal the same via cauterization.

In order to overcome male fears and phychological misgivings associated with surgical vasectomies, percutaneous vasectomy procedures have been developed for, in one case, cauterizing the vas deferens and, in another case, chemically sealing the vas deferens. U.S. Pat. No. 4,269,174 to Adair is an example of a percutaneous vasectomy method and apparatus is which the vas deferens of a male patient is cauterized without making a surgical incision in the scrotum wall. In the Adair patent a sharp-tipped, hollow needle which serves both as a first electrode and as a means by which an anesthetic is transferred from a container into the vas deferens, is inserted through the scrotum wall and into the interior of the vas deferens. After the anesthetic has been introduced into the vas deferens, the anesthetic container is removed from the needle, without withdrawing the needle from the vas deferens, and a second, blunt-tipped, electrode is inserted telescopically through the first needle into the vas deferens so as to protrude therefrom. Thereafter, the electrodes are energized with suitable cauterizing energy, sealing the vas deferens, and the two electrodes are then removed therefrom. The foregoing percutaneous vasectomy procedure has not proven to be entirely successful due to the fact that, in many cases, it fails to attain azoospermia. The high failure rate is believed to result from difficulty associated with placing the tip of the bipolar needle into the vas deferens since the bipolar needle has a diameter of about 1.6 mm and the average diameter of the lumen of the human vas deferens is about 0.55 mm, distendable to about 1.2 mm.

Yet another example of a percutaneous vasectomy procedure utilizing a cauterizing needle electrode which is inserted into the vas deferens is given in an article entitled "Percutaneous Fulgarization of Vas", by S. L. Agarwal, et al., in Indian Journal of Medical Research 78, October 1983, pp. 547–551 In this procedure a 4 cm long, 24 gauge, insulated vasectomy needle is inserted into the vas deferens and then the vas deferens is cauterized by diathermy coagulation current applied through the vasectomy needle, using an electrosurgical cautery. Detailed steps of the procedure are not provided in the article and difficulties with respect to accurate placement of the vasectomy needle electrode within the vas deferens and the amount of time expended in performing this procedure would result from its use.

An example of a percutaneous vasectomy procedure in which the vas deferens of a male patient is chemically occluded or sealed without making a surgical incision in the scrotum wall is given in an article entitled "Clinical Application of Vas Deferens Puncture", by Li Shun-qiang, in the Chinese Medical Journal, 93(1):69–70, 1980. The same procedure is apparently presented in greater detail in a report entitled "Non-Operative Sterility Research With Intravasal Injecting Drug (Clinical Report)", by Li Shun-qiang and Zhu Jin-Bo, presented at the Expert Committee Meeting on Training For Voluntary Surgical Contraception, Rio de Janeiro, Brazil, Sept. 26–29, 1984. In this procedure the vas deferens is, under local anesthesia, initially fixed with a clamp and a first, sharp-tipped, vas deferens puncture needle is inserted perpendicularly into the lumen of the vas deferens through its anterior wall. The first needle is then replaced by a second, blunt-tipped, vas deferens injection needle which is passed through the puncture hole of the first needle. Then, 0.02 ml of a chemical sealant mixture (e.g., carbolic acid-n-butyl-cyanacrylaty) is injected into the vas deferens through the second needle to obliterate the lumen permanently. After about 20 seconds, the mixture coagulates and the second needle is withdrawn.

Although satisfactory results appear to have been achieved with the chemical occlusion process described above, the necessity for extensive toxicology studies and regulatory agency approval of chemical agents injected into the human vas deferens represents a significant impediment to near term adoption and use of the procedure in many countries of the world.

It is, therefore, a primary object of the present invention to provide an improved, currently acceptable, method of sealing a male vas deferens without incising the wall of the patient's scrotum.

Another object of the present invention is to provide an improved percutaneous vasectomy method in which a puncture passageway is made from the outer surface of the scrotum to the interior of the vas defens by a sharp-tipped needle which is thereafter withdrawn and replaced in the passageway by a narrower, blunt-tipped, cauterizing needle.

Further objects and advantages of this invention will become apparent as the following description proceeds.

Briefly stated, and in accordance with one embodiment of this invention, the method of closing the vas deferens to sterilize a male patient without incising the patient's scrotum comprises the steps of inserting a sharp-tipped needle having a first predetermined diameter into the scrotum of the male patient and through a wall of the vas deferens, the insertion forming a passageway from the surface of the scrotum to the interior of the vas deferens; removing the sharp-tipped needle from the vas deferens and the scrotum; inserting a blunt-tipped needle having a second predetermined diameter, less than the first predetermined diameter, through the passageway and into the interior of the vas deferens; activating a cauterizing element which includes the blunt-tipped needle for a selected period of time to cauterize and thereby close the vas deferens to sterilize the male patient; and removing the blunt-tipped needle from the vas deferens and scrotum.

As used herein, the term "needle" has reference not only to conventional, hollow, injection type needles but also to solid trocar puncture needles.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIG. 5 is an elevation view, partly in section, of a hand held battery pack having a blunt-tipped electrode needle attached to an end thereof and in electrical circuit therewith; and, FIG. 6 is an elevation view, partly in section, showing a blunt-tipped needle having an optionally conductive fibre core which may be used in an alternative embodiment of this invention.

DETAILED DESCRIPTION OF THE INVENTION

Figure 1:
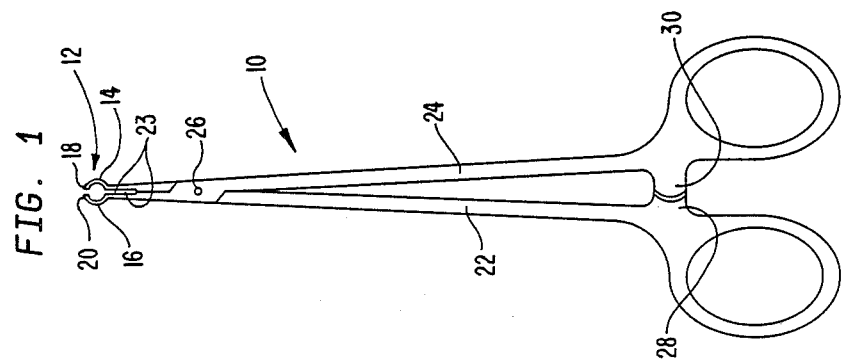
FIG. 1 is a plan view of a clamp used to clamp the scrotal skin tightly over the vas deferens thereby to fix the positions of the scrotal skin and vas deferens relative to one another.

Referring to FIG. 1, an extra-cutaneous vas deferens fixing clamp, shown generally at 10, has there been illustrated. The clamp 10 is a modified straight hemostat having at its distal end a ringed tip, shown generally at 12, which includes semi-circular ring portions 14 and 16 therein having respective blunt ends 18 and 20. The ends 18 and 20 are slightly spaced apart from each other (e.g., 0.5 mm) when the clamp 10 is in its fully clamped condition in order to prevent the ends 16 and 18 from exerting undue force on the scrotal skin positioned therebetween. The ring portions 14 and 16 are integrally connected to respective handle members 22 and 24 which are, in turn, pivotally connected to one another at 26. The handle members 22 and 24 carry respective, integral, interengaging clamp lock members 28 and 30 which interengage in a conventional manner to hold the clamp 10 in its locked position. The proximal ends of the ring portions 14 and 16 and the adjacent portions of handle members 22 and 24 are also separated slightly from one another, as shown at 23, when the clamp 10 is closed in order to avoid pinching the scrotal skin therebetween. Here again a transverse spacing of about 0.5 millimeters is provided. The inside diameter of the ringed tip 12 is preferably about 3.1 mm to enable it to encircle and clamp the scrotal skin tightly over the vas deferens to fix the positions of the scrotal skin and vas deferens relative to one another during the percutaneous vasectomy procedure, without exerting undue force on such body parts thereon.

Figure 2:
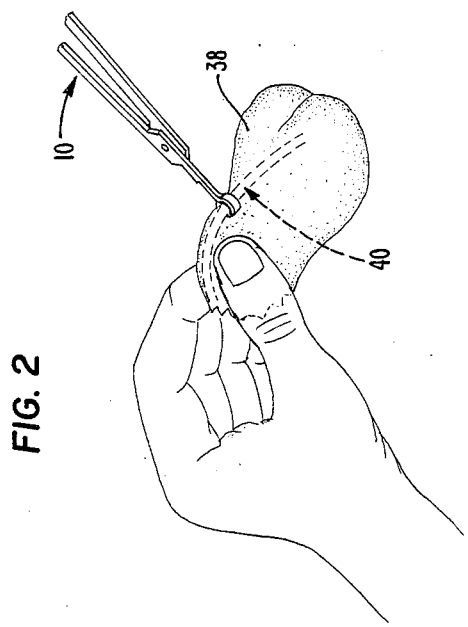
FIG. 2 is a fragmentary perspective view, showing the scrotum and vas deferens in a clamped, supported position preparatory to insertion of a sharp-tipped puncture needle through the scrotum wall and into the vas deferens.

Referring now to FIG. 2, the preliminary aspects of the percutaneous vasectomy procedure will now be considered. With the operator standing on the patient's right side, the right vas deferens is grasped over the index finger of the left hand and secured above and below with the thumb and middle finger in the median raphe of the mid-scrotum, as shown in FIG. 2. A local anesthetic, for example 2% lidocaine, is applied to the scrotal skin in the area above the raised vas deferens, for example by injecting sufficient lidocaine to create a 1 cm diameter skin wheal at that location and, without removing the local anesthetic needle, the peri-vasal tissue of the right vas deferens is infiltrated with 2½ cc of lidocaine. The local anesthetic needle is then removed and the left vas deferens grasped in an identical fashion and brought as superficially as possible under the median raphe, beneath the previously raised skin wheal. The local anesthetic needle is then reintroduced through the same hole previously used and the peri-vasal tissue on the left vas deferens is also infiltrated with 2½ cc of lidocaine. Then the local anesthetic needle is removed.

The ring portions 14 and 16 of the vas deferens fixing clamp 10 are then applied over, and encircle, both the exposed scrotal skin 38 and the underlying vas deferens, shown generally at 40, to tightly stretch the scrotal skin over the underlying vas deferens and fix the two parts together approximately 3 to 5 millimeters distal to the previously made needle puncture hole.

Figure 3:
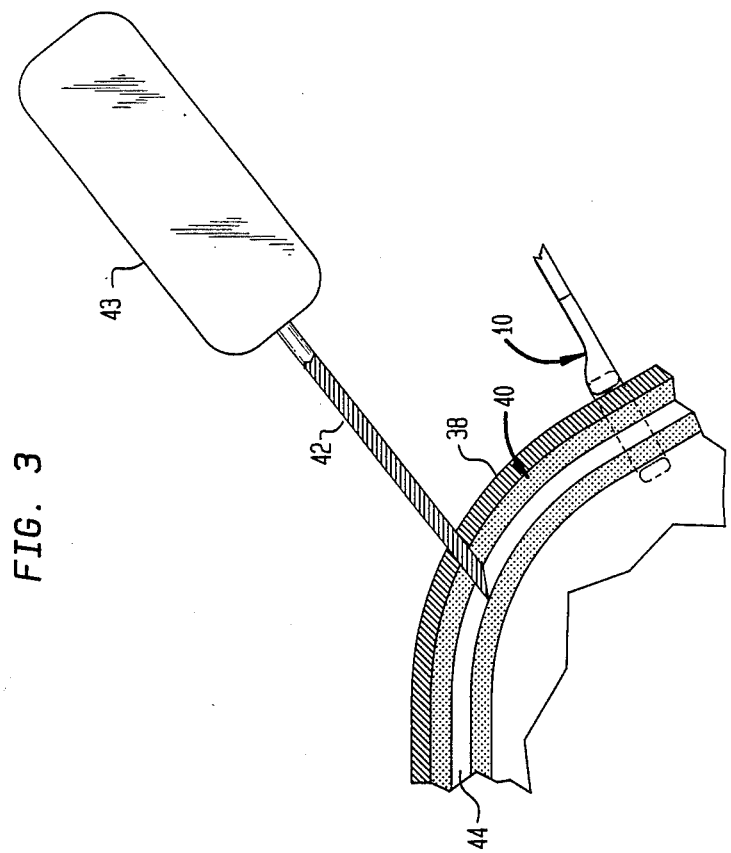
FIG. 3 is an enlarged, sectional view of a portion of the vas deferens shown in FIG. 2, illustrating the position of the puncture needle after it has passed through the wall of the scrotum and into the vas deferens.

Referring to FIG. 3, after fixation of the scrotal skin 38 and underlying vas deferens 40 by the clamp 10, the scrotal skin and the anterior wall of one of the vas deferens, for example the right one, is punctured with a 1 inch long, sharp-tipped, tipped, stainless steel puncture needle 42 of about 22-23 gage (approximately 0.8 mm external diameter) through the same puncture hole as was used for the introduction of the local anesthetic. The puncture needle 42 is preferably a solid trocar having a flattened handle portion 43 aligned with the pointed end of the needle so that when the handle 43 is held between the user's thumb and index finger, proper positioning of the tip of the needle relative to the anterior wall and lumen of the vas deferens is facilitated. The puncture needle 42, which alternatively may be a hollow needle if desired, is held almost perpendicular to the middle of the most prominent portion of the vas deferens 40 during puncture of the scrotum wall and anterior portion of the vas deferens, with the sharp-pointed tip thereof pointing toward the seminal vesicle side of the vas deferens, as shown in FIG. 3.

Figure 4:
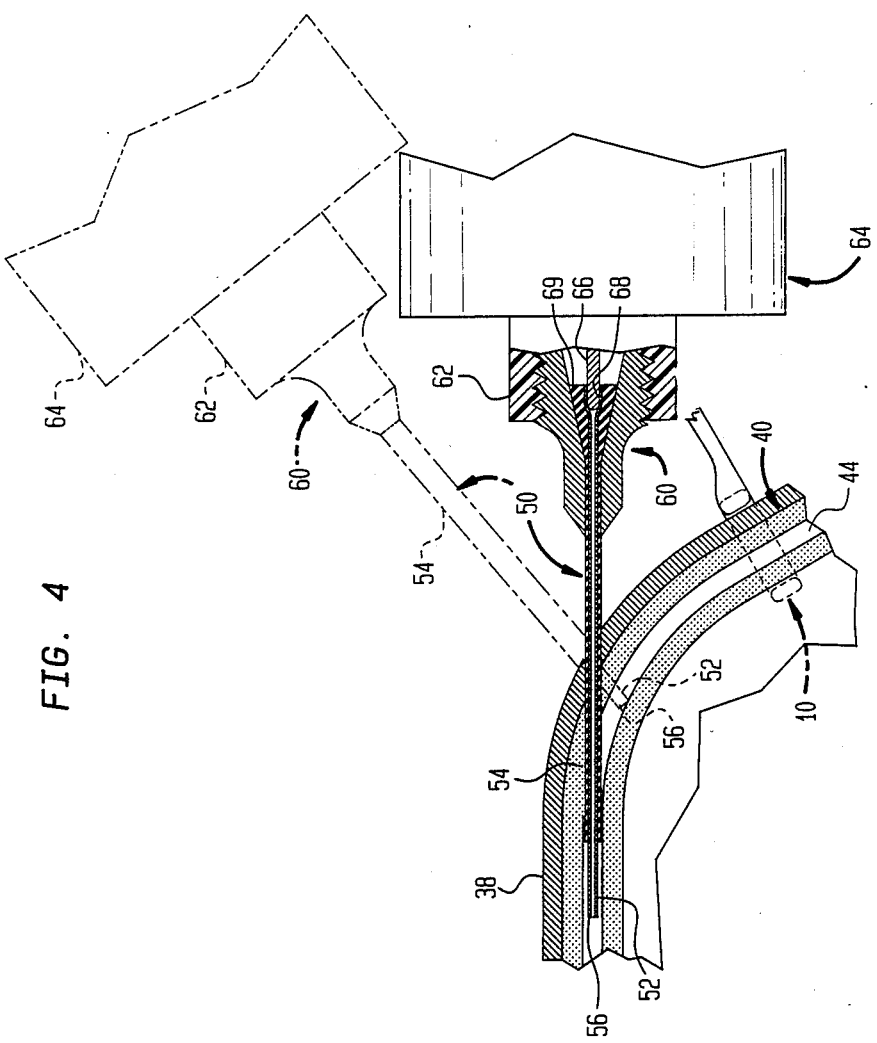
FIG. 4 is a fragmentary sectional view of the portion of the vas deferens shown in FIG. 3, showing the same after the puncture needle has been removed and replaced by a blunt-tipped electrode needle.

After penetrating the anterior wall and entering the lumen 44 of the vas deferens 40, the puncture needle 42 is removed and replaced immediately with a smaller diameter cauterizing needle, shown generally at 50 in FIG. 4. The cauterizing needle 50 is preferably a 1½ inch long, hollow, stainless steel cauterizing needle of about 24-25 gage (approximately 0.6 mm external diameter). The needle 50 preferably has had all but about a ¼ inch long tipped portion 52 thereof coated with an insulating material 54, for example a cold cured acrylic resin, and has been subsequently sterilized. The cauterizing needle 50 is inserted into the lumen 44 of the vas deferens 40 through the same passageway or puncture hole as was formed when the puncture needle 42 (FIG. 3) was inserted into the interior of the vas deferens 40. As shown by phantom lines in FIG. 4, the needle 50, which includes a blunt-tip 56 at the distal end thereof, is initially positioned at a right angle to the middle of the most prominent portion of the vas deferens 40, in the same manner as was the puncture needle 42 earlier. After penetrating the anterior wall of the vas deferens 40, and with the tip 56 within the lumen 44 the needle 50 is rotated to the position shown in full lines in FIG. 4, and is pushed further into the lumen 44 of the vas deferens, toward the seminal vesicle side thereof. If the penetration of the needle 50 is successful, the needle will slide easily into the lumen 44, with minimal resistance. The needle 50 is pushed sufficiently far into the lumen 44 so that the entire uninsulated tip portion 52 thereof is within the lumen and so that the insulated portion 54 of the needle 50 separates the metallic outer portion of the needle from the scrotal skin 38 and the puncture passageway through the anterior wall of the vas deferens 40.

Referring to FIG. 5, the cauterization needle 50 includes a proximal end portion, shown generally at 60, which is adapted to be threaded into a correspondingly threaded coupling 62 carried at one end of a hand held, portable, battery operated cauterizing element, or source of cauterization energy, shown generally at 64. The cauterizing element 64 comprises, for example, a VASECTOR model 4150, battery operated cauterizing unit made by Concept, Inc. of 12707 U.S. 19 South, Clearwater, Fla. 33546. The cauterizing element 64 is preferably modified to enable it to receive the threaded distal end 60 of the needle 50. The cauterizing element 64 includes an electrical contact or terminal 66 which, when the distal end 60 is threaded into the coupling 62, makes electrical contact with the stainless steel inner portion 68 of the cauterization needle 50. The stainless steel inner portion 68 of needle 50 is insulated from the threaded proximal end portion 60 of the needle by a layer of insulating material 69, which layer represents a continuation of the insulating material 54 surrounding a major portion of the length of the needle.

The cauterization needle 50, and particularly the uninsulated tip portion 52 thereof, constitutes a unipolar electrode which is used in conjunction with a grounding plate (not shown) that is connected by a conductor (not shown) to a second electrode (not shown) on the cauterizing element 64. In use, the ground plate is placed under, and in contact with, a portion of the patient's anatomy, for example the patient's leg. With the needle 50 within the lumen 44 of the patient's vas deferens 40, as shown in FIG. 4, a switch 65 on the cauterization element 64 is actuated and radio frequency cauterizing energy is applied from the cauterizing element 64, via the electrode 66, to the exposed tip portion 52 of needle 50, causing cauterization of the vas deferens. After sufficient cauterization, switch 65 is de-actuated, terminating the cauterization, and the needle 50 is withdrawn from the vas deferens 40 and scrotum 38. Thereafter, an identical procedure is used with respect to the other, or left, vas deferens to cauterize it, and the needle hole is covered with antibotic ointment.

As may be seen in FIG. 5, the internal surface of the proximal end portion 60 of needle 50 is generally conical in shape so that the needle may be attached to the distal tip portion of a syringe (not shown), with the container of the syringe in communication with the hollow central portion of the needle 50. This allows the operator to run various tests on the patient to insure that the needle 50 has been properly introduced into the lumen 44 of the vas deferens 50 and proper obliteration of the lumens of the right and left vas deferens has occurred. In connection with such tests, after the blunt needle 50 is inserted into the lumen 44 of the right vas deferens, toward the seminal vesicle side thereof, but before cauterization is initiated, 5 cc of, for example, 0.05% congo red is injected into the vas deferens from a syringe attached to the needle 50. After this injection, the syringe is removed, without removing the needle 50 from the vas deferens, filled with 4 cc of air and reattached to the needle. The assistant then firmly occludes the right vas deferens 2-3 cm from the puncture site, by pinching the same, while the operator similarly firmly occludes the right vas deferens around the needle 50, near its proximal end 60. The plunger of the syringe is then depressed to the 2 cc mark and held for 4 seconds and released. With successful puncture, the plunger returns to the 4 cc mark and any fluid remaining within the right vas deferens is aspirated. If the foregoing tests indicate successful cannulation of the lumen of the right vas deferens, the syringe is disconnected and the proximal end 60 of needle 50 is dried with gauze and then connected to the distal end of the cauterizing element 64. The aforementioned cauterization and occlusion of the right lumen of the vas deferens is then initiated.

An identical test method is used in connection with testing the lumen of the left vas deferens, except that 5 cc of 0.02% methylene blue is injected, instead of congo red. After test and cauterization procedures are completed and the needle hole is covered with antibiotic ointment, the patient is then asked to void. Brown urine indicates successful cannulation of both vas deferens; red urine indicates failure on the left side; and, green urine indicates failure on the right side. Undyed normal yellow urine indicates failure on both sides.

Referring to FIG. 6, an embodiment in which optical laser energy is used to cauterize the patient's vas deferens has there been illustrated. As used herein, the terms "cauterize", "cauterizing" and "cauterization" have reference not only to conventional cauterization, in which tissue surrounding an electrode is seared by radio frequency energy, optical laser energy or other forms of energy to the point at which various portions thereof adhere to one another to form an occlusion or blockage of the lumen of the vas deferens or other body parts, but they also have reference to the phenomenon resulting when optical laser energy or other energy is applied to tissue in sufficient amounts to coagulate or vaporize portions of the vas deferens or other body tissue. In the embodiment shown in FIG. 6, the needle 50 of FIG. 5 has been replaced by a narrow, blunt-tipped, stainless steel needle, shown generally at 70. The hollow central portion of needle 70 is filled with an optically conductive fiber or bundle of fibers 72 which extends beyond the distal end 74 of the stainless steel portion of the needle 70 a distance of approximately 0.5 cm. The fiber or bundle 72 is provided with a blunt distal end 76 thereon. The proximal end 78 of needle 70 is suitably coupled to a hand manipulatable element, shown generally at 80, which, in turn, is optically connected to a source of laser energy (not shown), controllable by the operator. Preferably, the needle 70 has an outer diameter of approximately 0.6 millimeters, similar to that of the outer diameter of the needle 50 of FIG. 5, and the needle 70 is inserted into the lumen 44 of the patient's vas deferens 40 in the same manner as was described earlier in connection with needle 50. A suitable source of optical laser energy is the Sharplan 2100 CW YAG laser, made by Sharplan Lasers Inc. of 1 Pearl Court, Allendale, N.J. 07401.

Although the foregoing discussion is concerned with the use of this invention in sterlizing a male human patient, it should be understood that other applications of the invention are possible, for example cauterizing body vessels other than the vas deferens. Additionally, the invention described herein may have utility in sterilizing female human patients and in cauterizing other female body vessels. Moreover the invention may be used in connection with cauterization of body vessels of animals.

From the foregoing description, it will be apparent that this invention provides an improved, currently acceptable, method of occluding the lumen of a male vas deferens without incising the wall of the patient's scrotum. The vas deferens is cauterized utilizing an improved percutaneous vasectomy procedure in which a puncture passageway is made from the outer surface of the scrotum to the interior of the vas deferens by a sharp-tipped puncture needle which is thereafter withdrawn and replaced in the passageway by a blunt-tipped, narrower, cauterizing needle.

While there have been shown and described what are presently considered to be the preferred embodiments of this invention, it will be obvious to those skilled in the art that various changes and modifications may be made without departing from the broader aspects of this invention. It is, therefore, aimed in the appended claims to cover all such changes and modifications as fall within the true spirit and scope of this invention.

What is claimed is:

1. A method of closing the vas deferens to sterilize a male patient without incising the patients scrotum, said method comprising the steps of:

Inserting a sharp-tipped needle having a first predetermined diameter into the scrotum of the male patient and through a wall of the vas deferens, said insertion forming a passageway from the surface of the scrotum to the interior of the vas deferens;

Removing said sharp-tipped needle from the vas deferens and the scrotum;

Inserting a blunt-tipped needle having a second predetermined diameter, less than said first predetermined diameter, said second diameter approximating the diameter of said vas deferens, through said passageway and into the interior of the vas deferens, whereby said blunt-tipped needle can readily slide within the lumen of said vas deferens;

Activating a cauterizing element which includes said blunt-tipped needle for a selected period of time to cauterize and thereby close the vas deferens to sterilize the male patient; and, Removing said blunt-tipped needle from the vas deferens and the scrotum.

2. A method according to claim 1, wherein said blunt-tipped needle is metallic and includes a coating of insulation material thereon throughout most of its length except for a distal portion thereof which is adapted to be positioned within the vas deferens, and wherein said cauterizing element is activated by radio frequency energy to cauterize the vas deferens.

3. A method according to claim 1, wherein said blunt-tipped needle comprises a rod-like, optically conductive element the distal end of which is adapted to be positioned within the vas deferens, and wherein said cauterizing element utilizes laser energy to cauterize the vas deferens.

4. A method according to any one of claims 1 to 3 which includes, prior to inserting said sharp-tipped needle into the scrotum, the further step of:

Injecting a local anesthetic into the scrotum and into the peri-vasal tissue therein to de-sensitize the same.

5. A method according to any one of claims 1 to 3 which includes, prior to inserting said sharp-tipped needle into the scrotum, the further steps of:

Injecting a local anesthetic into the scrotum and into the peri-vasal tissue therein to de-sensitize the same; and Clamping the scrotal skin tightly over the vas deferens to fix the positions of the scrotal skin and vas deferens relative to one another.

6. A method according to claim 1, wherein said blunt-tipped needle is hollow, said method including injecting a fluid through said hollow blunt-tipped needle to test for said cauterization without removing said blunt-tipped needle from said vas deferens.

* * * * *

UNITED STATES PATENT AND TRADEMARK OFFICE
CERTIFICATE OF CORRECTION

PATENT NO. : 4,920,982

DATED : May 1, 1990

INVENTOR(S) : Marc Goldstein

It is certified that error appears in the above-identified patent and that said Letters Patent is hereby corrected as shown below:

Column 1, line 6, "patent" should read --patient--.

Column 3, line 43, delete "optionally" and insert therefor --optically--.

Column 4, line 43, delete "tipped,".

Signed and Sealed this

Third Day of September, 1991

*Attest:*

HARRY F. MANBECK, JR.

*Attesting Officer*  *Commissioner of Patents and Trademarks*